US00PP13484P2

(12) United States Plant Patent
Austin

(10) Patent No.: US PP13,484 P2
(45) Date of Patent: Jan. 21, 2003

(54) SHRUB ROSE PLANT NAMED 'AUSWINTER'

(75) Inventor: David C. H. Austin, Albrighton (GB)

(73) Assignee: David Austin Roses Limited, Albrighton (GB)

( * ) Notice: Subject to any disclaimer, the term of this patent is extended or adjusted under 35 U.S.C. 154(b) by 36 days.

(21) Appl. No.: 09/712,310

(22) Filed: Nov. 13, 2000

(51) Int. Cl.[7] ..... A01H 5/00
(52) U.S. Cl. ..... Plt./104
(58) Field of Search ..... Plt./104

(56) References Cited

U.S. PATENT DOCUMENTS

PP9,008 P * 12/1994 Austin ..... Plt./104
PP9,705 P * 11/1996 Austin ..... Plt./104

OTHER PUBLICATIONS

UPOV–ROM GTITM Computer Database, GTI JOUVE retrieval software, citations for 'Auswinter' 2001/02.*

* cited by examiner

*Primary Examiner*—Bruce R. Campell
*Assistant Examiner*—W C Baker
(74) *Attorney, Agent, or Firm*—Klarquist Sparkman, LLP

(57) ABSTRACT

Shrub rose plant having tall bushy growth; quite large, neatly formed rosette shaped blossoms; very good disease resistance; and repeat flowering.

1 Drawing Sheet

1

The present invention relates to a new and distinct shrub rose plant which was originated by me by crossing an unnamed seedling with the variety AUScot.

The primary objective of this breeding was to produce a new rose variety that is disease resistant, tall, strong growing plant, with apricot orange, fully double blooms of an old fashioned shape, with a strong, fruity, tea rose fragrance, and that repeat flowers well throughout the summer. The objective was substantially achieved, along with other desirable improvements, as evidenced by the following unique combination of characteristics that are outstanding in the new variety and that distinguish it from its parents, as well as from all other varieties of which I am aware:

1. Tall, bushy, arching growth;
2. Quite large, neatly formed rosette shaped blooms with a strong, fruity tea rose fragrance;
3. Very good disease resistance; and
4. Repeat flowering.

Asexual reproduction of this new variety by budding, as performed at Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in color illustration of this character.

The following is a detailed description of my new rose cultivar with color descriptions using terminology in accordance with The Royal Horticultural Society (London) colour chart, except where ordinary dictionary significance of color is indicated.

2

Parentage:
*Seed Parent.*—Unnamed seedling.
*Pollen Parent.*—AUScot (U.S. Plant Pat. No. 7,215).
Classification:
*Botanical.*—*Rosa hybrida.*
*Commercial.*—Shrub.

FLOWER

Observations made in July, 1997 from three-year old specimens grown in a garden environment at Wolverhampton, England. The daily temperatures in Albrighton range from an average high in the mid-40's (°F.) and lows in the low 30's in the winter months to highs in the 60's and lows near 50 in the summer months. Average monthly duration of bright sunshine ranges from about 180 hours in the summer months to about 50 hours in the winter months.

Blooming Habit: Recurrent.
Bud:
*Size.*—About ½ to ¾ inches long when the petals start to unfurl.
*Form.*—The bud form is medium, pointed ovoid.
*Color.*—When sepals first divide, bud color is Orange Group 28C. When half blown, the upper sides of the petals are Orange Group 29A; and the lower sides of the petals are Orange Group 28C with Yellow-Orange Group 18B undertones.
*Sepals.*—Color: Yellow-Green Group 144A with Red-Purple Group 59A blush where exposed to bright sunlight. Surface texture: Slightly rough on appendaged sepals but smooth underneath. There are three normally appendaged sepals. There are 2 unappendaged sepals with hairy edges.

*Receptacle*.—Color: Yellow-Green Group 144A with Red-Purple Group 59B blush where exposed to bright sunlight. Shape: Pitcher. Size: Medium, about ½ inches by ½ inches. Surface: Smooth.

*Peduncle*.—Length: Medium, averaging about 1¾ inches. Surface: Rough, prickly. Color: Bronzy — Yellow-Green Group 145B with Red-Purple Group 59B overlay. Strength: Stiff.

Bloom:

*Size*.—Medium. Average open size is 3 to 3½ inches.

*Borne*.—Singly and in small clusters of up to four blooms having rounded shape.

*Stems*.—Strength: Strong. Average length is about 16–20 inches.

*Form*.—When first open: Cupped. Permanence: Flattens, outter petals curve back.

*Petalage*.—Number of petals under normal conditions: 120.

*Color*.—The upper sides of the petals are Yellow-Orange Group 21D at outer portions blending down to Yellow-Orange Group 19A in the middle of the petals and which extends to color spot at base. The reverse sides of the petals are Yellow-Orange Group 16C at outer ends blending to Yellow-Orange Group 15D in the middle of the petals and which extends to color spot at base. The base of each petal has Yellow Group 13B colorspot with Yellow Group 14A tip. The major color on the upper side is Yellow-Orange Group 20B.

*Variegations*.—None observed.

*Discoloration*.—The general tonality at the end of the first day: Yellow-Orange Group 20B. At the end of the third day: Paler, Yellow-Orange Group 19D.

*Fragrance*.—Strong, fruity fragrance of tea rose type.

Petals:

*Texture*.—Smooth.

*Shape*.—Round, pointed.

*Form*.—Edges slightly quilled.

*Arrangement*.—Quartered. Petaloids in the center are few and small.

*Persistence*.—Petals drop off cleanly before drying.

*Lastingness*.—On the plant: Long (about 7 days). As a cut flower: Not tested.

*Size*.—Length: 1.2–1.6 inches. Width: 1.0–1.6 inches.

Reproductive parts:

*Stamens*.—Number: 10–15 Anthers: Size: Medium. Color: Yellow Group 13B. Arrangement: Regular around styles. Filaments: Color: Yellow Group 9B. Pollen: Color: Yellow-Orange Group 17C.

*Pistils*.—Number: Average about 10. Styles: Color: Yellow Group 12B. Stigmas: Color: Yellow Group 9B.

*Hips*.—None formed.

Plant:

*Form*.—Large shrub, English.

*Growth*.—Vigorous, bushy. At maturity, height is 6 feet, width is 5 feet. Plant is mature at three years of age.

Foliage: Number of leaflets on normal mid-stem leaves: 5–7.

*Size*.—Medium (8 inches long×5 inches wide).

*Quantity*.—Normal.

*Color*.—New foliage: Upper surface: Green Group 137A with Greyed-Purple Group 187A blush. Lower surface: Green Group 137C with Greyed-Purple Group 187A blush. Old foliage: Upper surface: Yellow-Green Group 147A. Lower surface: Yellow-Green Group 147B.

Leaflets:

*Shape*.—Pointed oval, i.e., elliptic.

*Tip*.—Aristate.

*Base*.—Obtuse.

*Texture*.—Upper side: Semi-glossy. Under side: Matt.

*Edge*.—Serrated.

*Serration*.—Single, large.

*Petiole Rachis*.—Color: Reddish — Greyed-Purple Group 184A with Yellow-Green Group 144A undertones.

*Petiole Underside*.—Smooth with prickles.

*Stipules*.—Medium, serrated (about ¾ inches, long, wavy).

*Disease Resistance*.—Resistant to mildew, blackspot, and rust under normal growing conditions.

Wood:

*New Wood*.—Color: Greyed-Purple Group 183A with Green Group 143B undertone. Bark: Smooth.

*Old Wood*.—Color: Yellow-Green Group 146A. Bark: Smooth.

Prickles:

*Quantity*.—On main canes from base and laterals from main canes: One per two square inches.

*Position*.—Quite evenly distributed up the stem.

*Form*.—Medium, hooked downward. Underside: Concave. Upperside: Linear.

*Length*.—⅝ inch.

*Color when Young*.—Greyed-Purple Group 184B and Yellow-Green Group 144B undertone.

*Color when Mature*.—Geyed-Purple Group 187B.

Small Prickles:

*Quantity*.—On main stalks: Few. On laterals: None.

*Color*.—Greyed-Purple Group 187A.

*Length*.—¼ inch.

I claim:

1. A new and distinct variety of shrub rose plant of the *Rosa hybrida* class, substantially as herein shown and described, characterized particularly by its tall, bushy growth; quite large, neatly formed rosette shaped blooms with a strong fruity, tea rose fragrance; very good disease resistance; and repeat flowering.

* * * * *

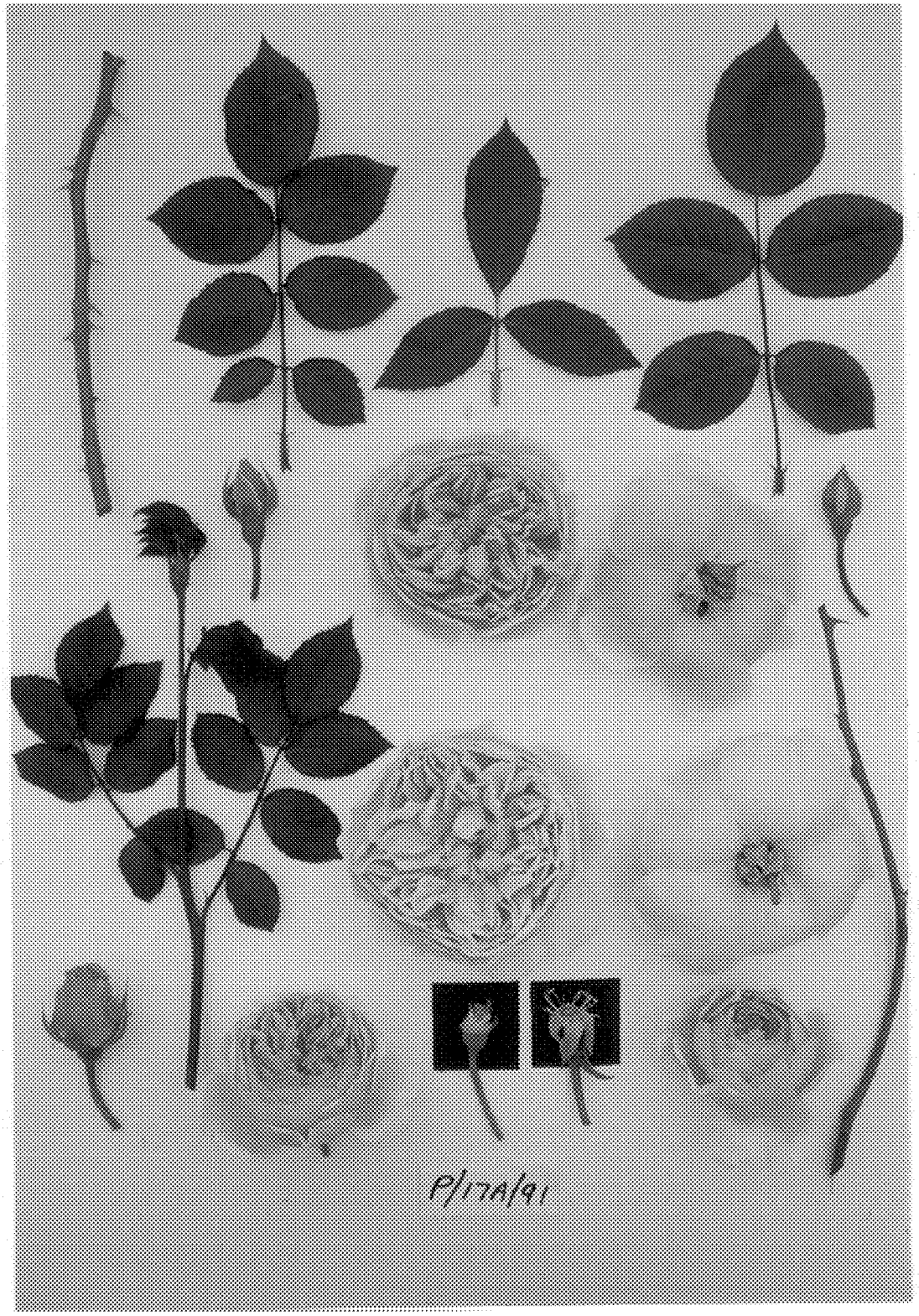
P/17A/91